United States Patent [19]

Minai

[11] Patent Number: 4,970,345
[45] Date of Patent: * Nov. 13, 1990

[54] PROCESS FOR PREPARING OXOCYCLOPENTENE DERIVATIVES

[75] Inventor: Masayoshi Minai, Moriyama, Japan

[73] Assignee: Sumitomo Chemical Company, Limited, Osaka, Japan

[*] Notice: The portion of the term of this patent subsequent to Apr. 9, 2002 has been disclaimed.

[21] Appl. No.: 831,067

[22] Filed: Feb. 20, 1986

Related U.S. Application Data

[63] Continuation of Ser. No. 737,590, Apr. 24, 1985, abandoned, which is a continuation of Ser. No. 270,556, Jun. 4, 1981, abandoned.

[30] Foreign Application Priority Data

Jun. 10, 1980 [JP] Japan .................................. 55-78529
Oct. 7, 1980 [JP] Japan .................................. 55-140787
Dec. 4, 1980 [JP] Japan .................................. 55-171523

[51] Int. Cl.$^5$ .......................................... C07C 45/00
[52] U.S. Cl. .................... 568/310; 568/341; 568/347; 568/315
[58] Field of Search ............... 568/361, 310, 341, 347, 568/315; 549/78

[56] References Cited

U.S. PATENT DOCUMENTS 4,510,329  4/1985  Saito et al. ........................... 568/361

OTHER PUBLICATIONS

Wagner & Zook "Synthetic Organic Chem.", (1965), pp. 32, 337, 338.
Tetrahedron, 34, 2775 (1978).
Piancatelli et al., *Tetrahedron Letters*, No. 39, pp. 3555–3558, (1976).
Piancatelli et al., *Tetrahedron Letters*, No. 13, pp. 1131–1134 (1977).

*Primary Examiner*—Alan Siegel
*Attorney, Agent, or Firm*—Birch, Stewart, Kolasch & Birch

[57] ABSTRACT

A process for preparing oxocyclopentenes of the formula:

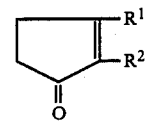

wherein $R^1$ is hydrogen, lower alkyl or lower alkenyl and $R^2$ is hydrogen, lower alkyl, lower alkenyl, lower alkynyl, substituted or unsubstituted aryl, ar(lower)alkyl, thienyl or cycloalkyl, which comprises subjecting a furan-carbinol of the formula:

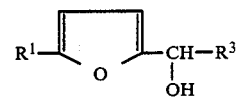

wherein $R^1$ is as defined above and $R^3$ is hydrogen, lower alkyl, lower alkenyl, lower alkynyl, substituted or unsubstituted aryl, ar(lower)alkyl, thienyl or cycloalkyl to rearrangement, subjecting the resultant hydroxycyclopentenone of the formula:

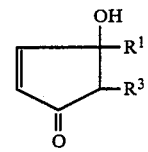

wherein $R^1$ and $R^3$ are each as defined above to hydrogenation and subjecting the resulting hydroxycyclopentanone of the formula;

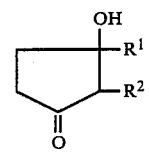

wherein $R^1$ and $R^2$ are each as defined above to dehydration.

1 Claim, No Drawings

PROCESS FOR PREPARING OXOCYCLOPENTENE DERIVATIVES

This application is a continuation, of application Ser. No. 737,590 filed on 4/24/85, now abandoned, which is a continuation of U.S. Pat. Ser. No. 270,556 filed on 6/4/81, now abandoned.

The present invention relates to a process for preparing oxocyclopentene derivatives. More particularly, it relates to a novel process for preparing oxocyclopentenes of the formula:

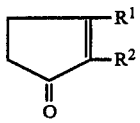
(I)

wherein $R^1$ is hydrogen, lower alkyl or lower alkenyl and $R^2$ is hydrogen, lower alkyl, lower alkenyl, substituted or unsubstituted aryl, ar(lower)alkyl, thienyl or cycloalkyl.

In the above significances, the term "lower" is intended to mean a group having not more than 8 carbon atoms. Thus, examples of lower alkyl are methyl, ethyl, n-propyl, isopropyl, n-butyl, isobutyl, n-pentyl, n-hexyl, n-heptyl, etc.; examples of lower alkenyl are allyl, α-methylallyl, α-ethylallyl, 4-pentenyl, 2,4-pentadienyl, 2-cis-butenyl, 2-cis-pentenyl, 2-trans-pentenyl, etc. The term "aryl" is intended to mean an aromatic group having not more than 18 carbon atoms, and examples thereof are phenyl, naphthyl, anthryl, etc. A substituent which is optionally present on the aryl group may be lower alkyl, lower alkoxy, halogen, etc. The term "cycloalkyl" is intended to mean groups having not more than 12 carbon atoms, and examples thereof include cyclopropyl, cyclopentyl, cyclohexyl, etc.

The said oxocyclopentenes (I) have various practical uses. For instance, they are useful as perfumes; particularly, jasmone (I: $R^1$=—$CH_3$; $R^2$=—$CH_2CH$=$CHCH_2CH_3$) is known as a perfume found in the volatile portion of oil from jasmine flowers. Further, for instance, they are useful as the starting materials in the production of cyclotene, ethylcyclotene, methyl jasmonate, methyl dihydrojasmonate, etc.

Among the oxocyclopentenes, the one of the formula (I) wherein $R^1$ is methyl and $R^2$ is n-pentyl (i.e. dihydrojasmone) has been produced by a procedure using levulic acid [J.Am.Chem.Soc., 66, 4 (1944)], a procedure using cyclotene [J.Org.Chem., 30, 1050 (1965)], a process using 1,4-diketone [Bull.Chem.Soc. Japan, 52, 1553 (1979)], etc. However, these conventional procedures are not satisfactory from the industrial viewpoint, because they require expensive starting materials and hardly available reagents, afford the desired product in poor yields, use troublesome operations, etc. Particularly, it is a great disadvantage common to them that the desired product is usually obtained together with by-products such as 3-hexyl-2-cyclopentenone, which can be eliminated from the desired product only with extreme difficulty.

As a result of an extensive study, it has now been found that the adoption of an entirely new route makes it possible to produce easily the oxocyclopentenes (I) such as dihydrojasmone in a high yield and a high purity. Thus, the present invention is based on the above finding and provides a novel process for preparing the oxocyclopentenes (I) which can be advantageously adopted in industry.

According to the present invention, the oxocyclopentene (I) can be produced from the corresponding furan-carbinol through the corresponding hydroxycyclopentenone and the corresponding hydroxycyclopentanone as shown in the following scheme:

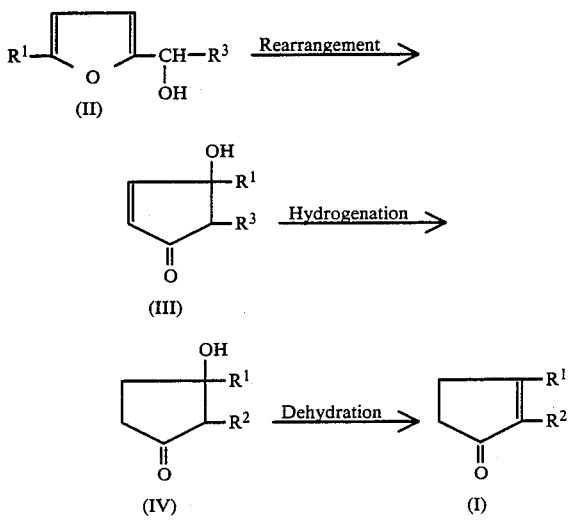

wherein $R^1$ and $R^2$ are each as defined above, and $R^3$ is hydrogen, lower alkyl, lower alkenyl, lower alkynyl, substituted or unsubstituted aryl, ar(lower)alkyl, thienyl or cycloalkyl.

The starting furan-carbinols (II) are per se known and can be produced, for instance, by reacting the corresponding 5-substituted furfural with a Grignard's reagent as shown in the following formulas:

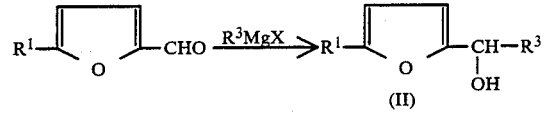

wherein $R^1$ and $R^2$ are each as defined above and X is halogen or by reacting the corresponding 2-substituted furan with an aldehyde in the presence of a basic catalyst as shown in the following formulas:

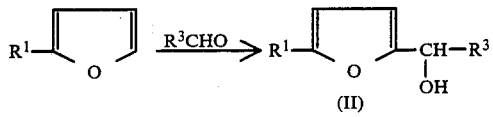

wherein $R^1$ and $R^3$ are each as defined above.

The rearrangement of the furan-carbinol (II) to the hydroxycyclopentenone (III) may be effected by treatment with water or a mixture of water and a divalent alcohol in the presence or absence of a catalyst.

As the reaction medium, there may be employed water or its mixture with a divalent alcohol. Examples of the divalent alcohol are ethylene glycol, 1,3-propanediol, 1,2-propanediol, 1,4-butanediol, 1,3-butanediol, etc. The proportion of water and the divalent alcohol may be usually 1 : 1–1/100 by weight, although any limitation is not present. The reaction medium may comprise any other organic solvent in addition to water or water and the divalent alcohol, provided that its amount is relatively small, e.g. less than about 10 % by weight. Examples of such organic solvent are methanol, ethanol, dioxane, tetrahydrofuran, dimethylformamide, dimethylsulfoxide, ethyl acetate, acetic acid, dichloroethane, toluene, acetone, methyl ethyl ketone, methyl isobutyl ketone, diethyl ether, etc.

The rearrangement can be achieved even in the absence of any catalyst. In general, however, the presence of a catalyst is favorable, because the reaction rate is increased and the conversion is enhanced. As the catalyst, there may be used metal salts such as phosphates, sulfates, chlorides, bromides, oxides, fatty acid salts and organic sulfonic acid salts of sodium, potassium, magnesium, zinc, iron, calcium, manganese, cobalt and aluminum, quaternary ammonium salts such as tetrabutylammonium bromide, benzyltrimethylammonium chloride, tricaprylmethylammonium chloride, dodecyltrimethylammonium chloride and caprylbenzyldimethylammonium chloride, surfactants such as higher fatty acid salts, polyoxyethylene alkylphenol ethers and higher fatty alcohols, etc. These catalysts may be used in an amount of 1/1000 to 5 parts by weight to one part by weight of the furan-carbinol (II), but they can be also used in any amount outside the said range. After completion of the rearrangement, the catalysts may be recovered from the reaction mixture and subjected to repeated use.

The rearrangement is usually performed at a pH between 3 and 7, preferably between 3.5 and 6.5. For adjusting the pH within the said range, there may be used acids such as organic acids (e.g. acetic acid, propionic acid, toluenesulfonic acid, methanesulfonic acid) and inorganic acids (e.g. hydrochloric acid, sulfuric acid, phosphoric acid, boric acid), bases such as organic bases (e.g. pyridine, triethylamine) and inorganic bases (e.g. sodium hydroxide, potassium carbonate, sodium hydrogen carbonate, dipotassium monohydrogen phosphate). Adjustment of the pH may be also achieved by the use of buffer solutions which contain dipotassium monohydrogen phosphate/ phosphoric acid, sodium acetate/acetic acid, sodium acetate/ phosphoric acid, phthalic acid/potassium carbonate, dipotassium monohydrogen phosphate/hydrochloric acid, monopotassium dihydrogen phosphate/potassium hydrogen carbonate, succinic acid/sodium hydrogen carbonate or the like. In general, it is favorable to avoid the use of strong acids (e.g. hydrochloric acid, hydrobromic acid) or strong bases (e.g. sodium hydroxide, potassium hydroxide) for adjustment of the pH.

The reaction temperature for the rearrangement is usually from 0° to 200° C., preferably from 20° to 160° C., especially from 70° to 140° C.

Recovery of the thus produced hydroxycyclopentenone (III) from the reaction mixture may be attained by per se conventional separation procedures such as extraction, fractionation, concentration and distillation. Alternatively, the reaction mixture containing the hydroxycyclopentenone (III) may be as such used in the subsequent step without separation of the hydroxycyclopentenone (III).

As to the rearrangement of the furan-carbinol (II) to the hydroxycyclopentenone (III), there is known a process wherein the former is treated in acetone including a small amount of water in the presence of zinc chloride [Tetrahedron, 34, 2775 (1978)]. In that process, however, the yield of the objective hydroxycyclopentenone (III) is extremely low. In the process of this invention, there is used water or its mixture with a divalent alcohol as the reaction medium so that the rearrangement is accomplished in an excellent yield.

The hydrogenation of the hydroxycyclopentenone (III) to the hydroxycyclopentanone (IV) may be achieved by a per se conventional procedure for reduction of an olefinic unsaturation such as catalytic hydrogenation or hydrogenation with an alkali metal.

In case of the catalytic hydrogenation, there may be used as the catalyst a palladium catalyst (e.g. palladium-carbon, palladium oxide, palladium chloride, Lindlar catalyst), platinum, Raney nickel, stabilized nickel, copper-chromium, ruthenium, rhodium-carbon, etc. The reaction can proceed in the absence of any solvent, but it is usually carried out in an inert solvent. The reaction temperature may be usually from −20° to 200° C., although this range is not essential.

In case of the hydrogenation with an alkali metal, the usable alkali metal is sodium, potassium, lithium, etc. Amalgamated alkali metals are also usable. The reaction is usually carried out in an inert solvent such as alcohols, amines and liquid ammonia. The reaction temperature is not limitative, and it may be usually from −60° to 150° C.

Recovery of the produced hydroxycyclopentanone (IV) from the reaction mixture may be accomplished by per se conventional separation procedures such as filtration, concentration and distillation. Alternatively, the reaction mixture comprising the hydroxycyclopentanone (IV) may be employed as such in the subsequent step without separation of the hydroxycyclopentanone (IV).

The dehydration of the hydroxycyclopentanone (IV) to the oxocyclopentene (I) may be accomplished by heating in the presence or absence of any catalyst.

As the catalyst, there may be used any acidic one which is conventionally employed in dehydration. Specific examples thereof include sulfuric acid, hydrochloric acid, acetic acid, acetic anhydride, phosphoric acid, polyphosphoric acid, phosphorus oxychloride, boric acid, boron trifluoride, toluenesulfonic acid, toluenesulfonyl chloride, etc. The amount of the catalyst is not limitative and may be usually from 1/500 to 1 part by weight to one part by weight of the hydroxycyclopentanone (IV). The use of any solvent is not necessary. If used, it is preferred to be an inert one which can form an azeotropic mixture with water, though other solvents are also usable. The reaction temperature is not limitative and may be usually from 0° to 200° C., preferably from 20° to 160° C.

By application of any per se conventional separation procedure such as concentration, fractionation and distillation of the reaction mixture, there is separated and recovered the oxocyclopentene (I).

In the above conversions, some side reactions may take place. However, it should be understood that such cases are within the scope of the invention, insofar as the major reactions intended and explained above proceed.

For instance, in the rearrangement of the furancarbinol (II) to the hydroxycyclopentenone (III), there may be by-produced the following 4-hydroxy-2-cyclopentenone depending on the reaction conditions such a the reaction time and the kind of the catalyst:

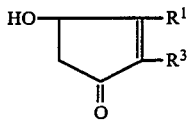

wherein $R^1$ and $R^3$ are each as defined above. However, the separation of this by-product from the reaction mixture or the reaction product is not needed, because it can be converted readily into the cyclopentenone of the formula:

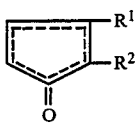

wherein $R^1$ and $R^2$ are each as defined above under the reaction conditions in the subsequent hydrogenation and dehydration steps. The cyclopentenone (VI) can be easily rearranged into the oxocyclopentene (I), and this rearrangement may be achieved simultaneously in the dehydration step depending upon the reaction condition as adopted.

Further, in the hydrogenation of the hydroxycyclopentenone (III) to the hydroxycyclopentanone (IV), any unsaturation bond which may be present in the substituent(s) represented by $R^1$ and/or $R^3$ may be simultaneously hydrogenated to a saturated or less unsaturated bond depending upon the reaction condition. For example, alkenyl or alkynyl represented by $R^1$ or $R^3$ may be converted into alkyl or alkenyl. In fact, the hydrogenation of the hydroxycyclopentenone (III: $R^1=R^3$=alkenyl) in the presence of an ordinary hydrogenation catalyst affords the hydroxycyclopentanone (IV: $R^1=R^2$=alkyl), but the hydrogenation in the presence of a Lindlar catalyst (e.g. palladium-lead-calcium carbonate, palladium-barium sulfate-quinoline) affords the hydroxycyclopentanone (IV: $R^1=R^2$=alkenyl). Further, the hydrogenation of the hydroxycyclopentenone (III: $R^3$=lower alkynyl) with a Lindlar catalyst gives the hydroxycyclopentanone (IV) wherein $R^2$ is alkenyl having a cis-configuration, while that with an alkali metal gives the hydroxycyclopentanone (IV) wherein $R^2$ is alkenyl having a trans-configuration.

As understood from the above, suitable reaction conditions may be chosen depending upon the kind of the desired product. For example, a Lindlar catalyst is effective in reducing an alkynyl group to an alkenyl group or reducing a double bond conjugated with a carbonyl group but is not effective in reducing an alkynyl group or an alkenyl group to an alkyl group. For the use of a Lindlar catalyst in the said effective cases, care should be taken to stop the reaction when the consumption of hydrogen reaches about 1 to 1.1 equivalent with respect to the starting compound for attaining a satisfactory selectivity. Further, for example, the reduction with an alkali metal is effective for selective reduction of a double bond conjugated with a carbonyl group when an appropriate reaction condition is selected.

Still, among the hydroxycyclopentanones (IV) prepared by the process of this invention, those wherein $R^1$ is hydrogen, lower alkyl or lower alkenyl and $R^2$ is hydrogen, lower alkyl, lower alkenyl, cycloalkyl, substituted or unsubstituted aryl or ar(lower)alkyl, except the case wherein both $R^1$ and $R^2$ are hydrogen, are novel. These compounds are useful as intermediates in the synthesis of medicines and agro-chemicals. They are also useful as intermediates in the synthesis of oxocyclopentene derivatives such as dihydrojasmone and jasmone.

Practical and presently preferred embodiments of the invention are illustratively shown in the following examples wherein part(s) is by weight.

EXAMPLE 1

Into a four necked flask equipped with an agitator and a thermometer, 5-methyl-α-n-propyl-furfuryl alcohol (40 parts) and water (1200 parts) were charged, and the resultant mixture was stirred at a temperature of 95° to 100° C. in a nitrogen stream, during which the pH was maintained at 4.9 to 5.3. After confirming the complete consumption of the starting compound by gas chromatography, the reaction mixture was cooled and extracted with methyl isobutyl ketone. The extract was concentrated to give 2-n-propyl-3-hydroxy-3-methyl-4-cyclopentenone in a yield of 81 %.

The above obtained hydroxycyclopentenone (30 parts), 5 % palladium-carbon (0.3.part), water (10 parts) and ethanol (60 parts) were charged into an autoclave, and the resultant mixture was subjected to catalytic hydrogenation under a hydrogen pressure of 2 to 5 kg/cm² at a temperature of 20° to 30° C. for 3 hours. The reaction mixture was filtered, and the filtrate was concentrated to give 2-n-propyl-3-hydroxy-3-methylcyclopentanone ($n_D^{21}$ 1.4676) in a yield of 98%.

A mixture of the above obtained hydroxycyclopentanone (25 parts) and p-toluenesulfonic acid (1.25 parts) in benzene (75 parts) was refluxed for 1 hour, during which by-produced water was eliminated by azeotropic distillation. The organic phase was washed with an alkali and water and concentrated. The residue was distilled to give 2-n-propyl-3-methyl-2-cyclopentenone (b.p., 60°-65° C./3-5 mmHg) in a yield of 94 %.

EXAMPLE 2

In the same apparatus as in Example 1, 5-methyl-allyl-furfuryl alcohol (50 parts) and a buffer solution prepared from water (1500 parts) and dipotassium monohydrogen phosphate (1.7 parts) and adjusted to pH 5.1 with phosphoric acid were charged, and the resultant mixture was stirred at 100° C. in a nitrogen stream until the starting compound was consumed. The reaction mixture was treated as in Example 1 to give 2-allyl-3-hydroxy-3-methyl-4-cyclopentenone in a yield of 80 %.

The above obtained hydroxycyclopentenone (35 parts), Lindlar catalyst (0.7 part) and isopropanol (70 parts) were charged into an autoclave, and the resultant mixture was subjected to catalytic hydrogenation under a hydrogen pressure of 1 to 3 kg/cm² until the absorbed amount of hydrogen reached 1.05 equivalent with respect to the starting compound. The reaction mixture was treated as in Example 1 to give 2-allyl-3-hydroxy-3-methylcyclopentanone ($n_D^{20}$ 1.4661) in a yield of 85 %.

A mixture of the above obtained hydroxycyclopentanone (25 parts) and sulfuric acid (0.5 part) in benzene (100 parts) was refluxed. The reaction mixture was treated as in Example 1 to give 2-allyl-3-methyl-2-cyclopentenone in a yield of 97 %.

EXAMPLE 3

In the same apparatus as in Example 1, 5-methyl-α-2-cis-pentenyl)-furfuryl alcohol (30 parts), ethylene glycol (60 parts) and a buffer solution prepared from water (1200 parts) and dipotassium monohydrogen phosphate (1 part) and adjusted to pH 5.0 with phosphoric acid were charged, and the resultant mixture was stirred at 100° C. until the starting compound was consumed. The reaction mixture was treated as in Example 1 to give 2-(2-cis-pentenyl)-3-hydroxy-3-methyl-4-cyclopentenone in a yield of 74 %.

The above obtained hydroxycyclopentenone (20 parts), Lindlar catalyst (0.6 part) and ethanol (40 parts) were charged into an autoclave, and the resultant mixture was subjected to catalytic hydrogenation at 20° C. under a hydrogen pressure of 1 kg/cm$^2$ until the absorbed amount of hydrogen reached 1.1 equivalent with respect to the starting compound. The reaction mixture was treated as in Example 1 to give 2-(2-cis-pentenyl)-3-hydroxy-3-methylcyclopentanone ($n_D^{25}$ 1.4690) in a yield of 85 %.

A mixture of the above obtained hydroxycyclopentanone (15 parts) and boric acid (0.75 part) in benzene (45 parts) was refluxed. The reaction mixture was treated as in Example 1 to give 2-(2-cis-pentenyl)-3-methyl-2-cyclopentenone in a yield of 98 %.

EXAMPLE 4

In the same apparatus as in Example 1, α-n-pentylfurfuryl alcohol (30 parts) and water (1500 parts) were charged, and the resultant mixture was stirred at a temperature of 100° C. for 35 hours, during which the pH was maintained at 4.6 to 5.0. The reaction mixture was treated as in Example 1 to give a mixture of 2-n-pentyl-3-hydroxy-4cyclopentenone and 2-n-pentyl-4-hydroxy-2-cyclopentenone in a yield of 86 %.

The above obtained mixture (20 parts), Raney nickel (1 part), water (15 parts) and ethanol (60 parts) were charged into an autoclave, and the resultant mixture was subjected to catalytic hydrogenation under a hydrogen pressure of 2 to 5 kg/cm$^2$ at a temperature of 25° to 35° C. The reaction mixture was treated as in Example 1 to give a mixture of 2-n-pentyl-3-hydroxycyclopentanone and 2-n-pentyl-4-hydroxycyclopentanone in a yield of 97 %.

The above prepared mixture (18 parts) was admixed with p-toluenesulfonic acid (0.9 part) and xylene (54 parts) and refluxed for 2 hours, during which by-produced water was eliminated by azeotropic distillation. The reaction mixture was treated as in Example 1 to give 2-n-pentyl-2-cyclopentenone in a yield of 96 %.

EXAMPLE 5

Into an autoclave equipped with a stirrer and a thermometer, α-n-hexyl-furfuryl alcohol (40 parts) and a buffer solution prepared from water (1600 parts) and sodium acetate (1 part) and adjusted to pH 4.8 with phosphoric acid were charged, and the resultant mixture was stirred at 110 to 120° C. until the starting compound was consumed. The reaction mixture was cooled and treated as in Example 1 to give a mixture of 2-n-hexyl-3-hydroxy-4-cyclopentenone and 2-n-hexyl-4-hydroxy-2-cyclopentenone in a yield of 84%.

To the above obtained mixture (30 parts), 5 % palladium-carbon (0.6 part) and toluene (90 parts) were added, and the resultant mixture was subjected to catalytic hydrogenation under a hydrogen pressure of 3 to 6 kg/cm$^2$ at a temperature of 30° to 50° C. The reaction mixture was filtered, and the filtrate was concentrated to give a mixture of 2-n-hexyl-3-hydroxycyclopentanone and 2-n-hexyl-4-hydroxycyclopentanone in a yield of 98 %.

The above prepared mixture (25 parts) was admixed with p-toluenesulfonic acid (1.25 parts) and toluene (75 parts) and refluxed for 2 hours, during which by-produced water was eliminated by azeotropic distillation. The reaction mixture was treated as in Example 1 to give 2-n-hexyl-2-cyclopentenone in a yield of 97 %.

EXAMPLES 6 to 12

In the same manner as above, the rearrangement of the furan-carbinol (II) to the hydroxycyclopentenone (III), the hydrogenation of the hydroxycyclopentenone (III) to the hydroxycyclopentanone (IV) and the dehydration of the hydroxycyclopentanone (IV) to the oxocyclopentene (I) were carried out. The results are shown in Table 1 (rearrangement), Table 2 (hydrogenation) and Table 3 (dehydration).

TABLE 1

| Example | Furan-carbinol (II) R$^1$ | R$^2$ | Catalyst Material | Amount*$^1$ | Solvent Material | Amount*$^1$ | pH | Reaction temp. (°C.) | Yield (%)*$^2$ |
|---|---|---|---|---|---|---|---|---|---|
| 6 | CH$_3$ | 3-cis-Hexenyl | Dipotassium monohydrogen phosphate/phosphoric acid | 1/30 | Water | 40 | 5.1 | 100 | 77 |
|   |   |   | Boric acid | 1/50 |   |   |   |   |   |
| 7 | CH$_3$ | 2-Pentynyl | — | — | Water | 40 | 4.9–5.3 | 100 | 82 |
| 8 | CH$_3$ | Cyclohexyl | Sodium acetate/acetic acid | 1/50 | Water | 40 | 5.2 | 100 | 76 |
| 9 | CH$_3$ | Phenyl | Emulgen 910*$^3$ | 1/30 | Water | 30 | 4.7–5.4 | 100 | 70 |
|   |   |   |   |   | Ethylene glycol | 15 |   |   |   |
| 10 | H | —CH$_2$C≡CH | Tetrabutylammonium bromide | 1/50 | Water | 20 | 4.9–5.1 | 100 | 74 |
| 11 | H | 2-cis-Pentenyl | Dipotassium monohydrogen phosphate/phosphoric acid | 1/30 | Water | 40 | 5.2 | 110–120 | 81 |
| 12 | H | Benzyl | Dipotassium monohydrogen phosphate/phosphoric acid | 1/20 | Water | 40 | 4.9 | 120 | 76 |

TABLE 1-continued

| Ex- ample | Furan-carbinol (II) $R^1$ | $R^2$ | Catalyst Material | Amount*[1] | Solvent Material | Amount*[1] | pH | Reaction temp. (°C.) | Yield (%)*[2] |
|---|---|---|---|---|---|---|---|---|---|
| | | | Boric acid | 1/30 | | | | | |

Note:
*[1] Amount (part(s)) to one part of the furan-carbinol (II)
*[2] Yield of the hydroxycyclopentenone (III) and its isomer (V)
*[3] Polyoxyethylene nonylphenyl ether; manufactured by Kao Atlas Co.

TABLE 2

| Ex- ample | Hydroxycyclopentenone (III) $R^1$ | $R^3$ | Catalyst (amount)*[1] | Solvent (amount)*[1] | Reaction condition | Hydroxycyclopentanone (IV) $R^1$ | $R^2$ | Yield (%) |
|---|---|---|---|---|---|---|---|---|
| 6 | $CH_3$ | 3-cis-Hexenyl | 5% Palladium-carbon (1/50) | Toluene (3) | Hydrogen pressure, 5–6 kg/cm²; 20–40° C.; 3 hours | $CH_3$ | n-Hexyl | 97 $n_D^{20}$ 1.4697 |
| 7 | $CH_3$ | 2-Pentynyl | Lindlar catalyst (1/30) | Ethanol (3) | Hydrogen pressure, 1–2 kg/cm²; 20° C.; absorbed amount of hydrogen, 2.1 equivalents | $CH_3$ | 2-cis-Pentenyl | 83 |
| 8 | $CH_3$ | Cyclohexyl | 5% Palladium-carbon (1/50) | Isopropanol (2) | Hydrogen pressure, 4–5 kg/cm²; 30–40° C.; 2 hours | $CH_3$ | Cyclohexyl | 98 $n_D^{23}$ 1.4730 |
| 9 | $CH_3$ | Phenyl | 5% Palladium-carbon (1/50) | Isopropanol (2) Water (0.5) | Hydrogen pressure 4–5 kg/cm² 30–40° C.; 2 hours | $CH_3$ | Phenyl | 97 $n_D^{21}$ 1.4803 |
| 10 | H | $-CH_2C \equiv CH$ | Lindlar catalyst (1/30) | Ethanol (3) Water (1) | Hydrogen pressure, 1–2 kg/cm²; 20° C.; absorbed amount of hydrogen, 2.2 equivalents | H | $CH_2CH=CH_2$ | 84 |
| 11 | H | 2-cis-Pentenyl | Lindlar catalyst (1/30) | Toluene (3) | Hydrogen pressure, 1–2 kg/cm²; 20° C.; absorbed amount of hydrogen, 1.1 equivalents | H | 2-cis-Pentenyl | 86 |
| 12 | H | Benzyl | 5% Palladium-carbon (1/30) | Ethanol (3) | Hydrogen pressure, 2–5 kg/cm²; 30–40° C.; 2 hours | H | Benzyl | 96 $n_D^{20}$ 1.5012 |

Note:
*[1] Amount (part(s)) to one part of the hydroxycyclopentenone (III)

TABLE 3

| Ex- ample | Hydroxycyclopentanone (IV) $R^1$ | $R^2$ | Acid (amount)*[1] | Solvent (amount)*[1] | Reaction condition | Yield of oxo-cyclopentene (I) (%) |
|---|---|---|---|---|---|---|
| 6 | $CH_3$ | n-Hexyl | Sulfuric acid (1/50) | Benzene (3) | Refluxing for 1 hour | 98 |
| 7 | $CH_3$ | 2-cis-Pentenyl | p-Toluenesulfonic acid (1/50) | Benzene (3) | Refluxing for 1 hour | 97 |
| 8 | $CH_3$ | Cyclohexyl | p-Toluenesulfonic acid (1/30) | Toluene (3) | Refluxing for 1 hour | 98 |
| 9 | $CH_3$ | Phenyl | Boric acid (1/20) | Benzene (4) | Refluxing for 3 hours | 96 |
| 10 | H | $CH_2CH=CH_2$ | p-Toluenesulfonic acid (1/20) | Toluene (3) | Refluxing for 2 hours | 98 |
| 11 | H | 2-cis-Pentenyl | p-Toluenesulfonic acid (1/20) | Toluene (3) | Refluxing for 2 hours | 97 |
| 12 | H | Benzyl | p-Toluenesulfonic acid (1/30) | Toluene (3) | Refluxing for 2 hours | 95 |

Note:
*[1] Amount (part(s)) to one part of the hydroxycyclopentanone (IV)

EXAMPLE 13

In the same apparatus as in Example 1, 5-methyl-α-methyl-furfuryl alcohol (35 parts), water (1050 parts) and sodium acetate (0.07 part) were charged, and the resultant mixture was stirred at 100° C. in a nitrogen stream while maintaining the pH at 5.0 to 5.7 until the starting compound was consumed. The reaction mixture was treated as in Example 1 to give 2-methyl-3-hydroxy-3-methyl-4-cyclopentenone in a yield of 78 %.

The above obtained hydroxycyclopentenone (20 parts), the stabilized nickel (0.6 part) and toluene (80 parts) were charged into an autoclave, and the resultant mixture was subjected to catalytic hydrogenation under a hydrogen pressure of 1 to 3 kg/cm². The reaction mixture was treated as in Example 1 to give 2-methyl-3-hydroxy-3-methylcyclopentanone in a yield of 98 %.

A mixture of the above obtained hydroxycyclopentanone (15 parts) and phosphoric acid (0.45 part) in toluene (45 parts) was refluxed for 3 hours, during which by-produced water was eliminated by azeotropic distillation. The reaction mixture was treated as in Example 1 to give 2,3-dimethyl-2-cyclopentenone in a yield of 98 %.

EXAMPLE 14

In the same apparatus as in Example 1, α-ethylfurfuryl alcohol (50 parts), water (1000 parts) and calcium chloride (0.02 part) were charged, and the resultant mixture was stirred at 100° C. in nitrogen stream for 30 hours, during which the pH was maintained at 4.6 to 6.5. Water was removed by evaporation, and the residue was extracted with methyl isobutyl ketone. The extract was concentrated to give a mixture of 2-ethyl-3-hydroxy-4-cyclopentenone and 2-ethyl-4-hydroxy-2-cyclopentenone in a yield of 82%.

To the above obtained mixture (35 parts), 5 % palladium-carbon (0.7 part), water (35 parts) and isopropanol (140 parts) were added, and the resultant mixture was subjected to catalytic hydrogenation at room temperature. The reaction mixture was treated as in Example 1 to give a mixture of 2-ethyl-3-hydroxycyclopentanone and 2-ethyl-4-hydroxycyclopentanone in a yield of 97 %.

The above prepared mixture (30 parts) was admixed with p-toluenesulfonic acid (0.6 part) and benzene (90 parts) and refluxed for 1 hour, during which by-produced water was eliminated by azeotropic distillation. The reaction mixture was washed with 1 % sodium hydroxide solution and water in order. The organic layer was concentrated, and the residue was admixed with methanol and 10 % sodium hydroxide solution respectively in amounts of 3 times and 1/50 time on the weight of the residue and refluxed for 30 minutes. The reaction mixture was poured into water and extracted with hexane. The extract was washed with water and concentrated to give 2-ethylcyclopentenone in a yield of 95 %.

EXAMPLE 15

In the same apparatus as in Example 1 5-methyl-α-n-pentyl-furfuryl alcohol (40 parts), ethylene glycol (20 parts) and a buffer solution prepared from water (1200 parts) and sodium acetate (0.5 part) and adjusted to pH 5.2 with acetic acid were charged, and the resultant mixture was stirred at 100° C. in a nitrogen stream for 20 hours. The reaction mixture was cooled and extracted with toluene. The extract was concentrated to give 2-n-pentyl-3-hydroxy-3-methyl-4-cyclopentenone in a yield of 84 %.

The thus obtained hydroxycyclopentenone (30 parts) was admixed with 5 % palladium-carbon (0.3 part), water (15 parts) and ethanol (60 parts), and the resultant mixture was subjected to catalytic hydrogenation in an autoclave under a hydrogen pressure of 2 to 5 kg/cm$^2$ for 3 hours. After separation of the catalyst by filtration, the filtrate was concentrated to give 2-n-pentyl-3-hydroxy-3-methylcyclopentanone (n$_D^{21}$ 1.4685) in a yield of 98 %.

A mixture of the above obtained hydroxycyclopentanone (25 parts), toluenesulfonic acid (1.25 parts) and benzene (75 parts) was refluxed for 1 hour, during which by-produced water was eliminated by azeotropic distillation. The organic phase was separated, washed with an alkali and water and concentrated. The residue was distilled to give dihydrojasmone (b.p., 109–111° C./5–6 mmHg) in a yield of 96 %.

EXAMPLE 16

In the same apparatus as in Example 1, furfuryl alcohol (40 parts) and a buffer solution prepared from water (1200 parts) and dipotassium monohydrogen phosphate (1 part) and adjusted to pH 4.1 with phosphoric acid were charged, and the resultant mixture was stirred at 100° C. in a nitrogen stream until the starting compound was consumed. The reaction mixture was treated as in Example 14 to give 3-hydroxy-4-cyclopentenone in a yield of 75 %.

In the similar manner to Example 1, the above obtained hydroxycyclopentenone was converted into 2-cyclopentenone in a yield of 93 %.

EXAMPLE 17

In the same apparatus as in Example 1, 5-methylfurfuryl alcohol (40 parts) and water (1200 parts) were charged, and the resultant mixture was stirred at 100° C. in a nitrogen stream for 30 hours, during which the pH was adjusted to 3.6 to 5.0. The reaction mixture was treated as in Example 14 to give a mixture of 3-hydroxy-3-methyl-4-cyclopentenone and 3-methyl-4-hydroxy-2-cyclopentenone in a yield of 55 %.

In the similar manner to Example 14, the above obtained hydroxycyclopentenone was subjected to hydrogenation, dehydration and rearrangement (isomerization) to give 3-methyl-2-cyclopentenone in a yield of 94 %.

EXAMPLE 18

In the same apparatus as in Example 1, α-n-hexylfurfuryl alcohol (30 parts) and water (1500 parts) were charged, and the resultant mixture was stirred at 100° C., during which the pH was maintained at 4.6 to 5.0 until the starting compound was consumed. The reaction mixture was treated as in Example 1, followed by purification with chromatography to give 2-n-hexyl-3-hydroxy-4-cyclopentenone in a yield of 65 %.

The thus obtained hydroxycyclopentenone (15 parts), 5 % palladium-carbon (0.3 part), water (15 parts) and isopropanol (60 parts) were charged into an apparatus, and hydrogen was introduced therein at room temperature under ordinary pressure. After completion of the reaction, the catalyst was separated by filtration. From the filtrate, there was obtained 2-n-hexyl-3-hydroxycyclopentanone (n$_D^{23}$ 1.4677) in a yield of 97 %.

EXAMPLE 19

In the same apparatus as in Example 1, c-methylfurfuryl alcohol (50 parts) and water (1200 parts) were charged, and the resultant mixture was stirred at 100° C. in a nitrogen stream while maintaining the pH at 4.7 to 5.2 until the starting compound was consumed. The reaction mixture was treated as in Example 14 to give a mixture of 2-methyl-3-hydroxy-4-cyclopentenone and 2-methyl-4-hydroxy-2-cyclopentenone in a yield of 85 %.

To the above obtained mixture (40 parts), 5 % palladium-carbon (1 part), water (60 parts) and ethanol (120 parts) were added, and the resultant mixture was subjected to catalytic hydrogenation in an autoclave under a hydrogen pressure of 1 to 2 kg/cm$^2$ for 2 hours. After separation of the catalyst by filtration, the filtrate was concentrated to give a mixture of 2-methyl-3-hydroxycyclopentanone and 2-methyl-4-hydroxycyclopentanone in a yield of 98 %.

In the similar manner to Example 14, the above obtained hydroxycyclopentanone was subjected to dehydration and rearrangement (isomerization) to give 2-methyl-2-cyclopentenone in a yield of 95 %.

What is claimed is:

1. A process for preparing an oxocyclopentene of the formula:

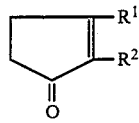

wherein $R^1$ is hydrogen, lower alkyl or lower alkenyl and $R^2$ is hydrogen, lower alkyl, lower alkenyl, cycloalkyl or ar (lower) alkyl, which comprises:

(a) subjecting a furan-carbinol of the formula:

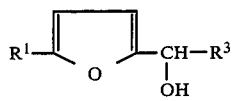

wherein $R^1$ is as defined above and $R^3$ is hydrogen, lower alkyl, lower alkenyl, lower alkynyl, cycloalkyl or ar (lower) alkyl to rearrangement in a solvent consisting essentially of water or a mixture of water and a divalent alcohol and adjusting the pH between 3.5 to 6.5:

(b) hydrogenating the resulting hydroxycyclopentenone of the formula:

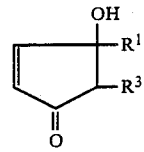

wherein $R^1$ AND $R^3$ are each as defined above by catalytic hydrogenation in the presence of a palladium catalyst, Raney nickel, stabilized nickel or rhodium-carbon, or by the use of an alkali metal; and (c) dehydrating the resulting hydroxycyclopentenone of the formula:

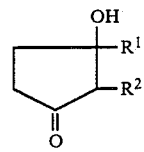

wherein $R^1$ and $R^2$ are each as defined above in the presence or in the absence of an acidic catalyst.

* * * * *